(12) United States Patent
Paris et al.

(10) Patent No.: US 6,631,020 B2
(45) Date of Patent: Oct. 7, 2003

(54) SCANNING DEVICE FOR A LASER BEAM FOCUS

(75) Inventors: Jacques Paris, Bagnols/Ceze (FR); Patrick Rouannet, Pont Saint-Esprit (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/169,735

(22) PCT Filed: Jan. 16, 2001

(86) PCT No.: PCT/FR01/00127
§ 371 (c)(1),
(2), (4) Date: Jul. 16, 2002

(87) PCT Pub. No.: WO01/53873
PCT Pub. Date: Jul. 26, 2001

(65) Prior Publication Data
US 2003/0011859 A1 Jan. 16, 2003

(30) Foreign Application Priority Data
Jan. 17, 2000 (FR) ............................................. 00 00505

(51) Int. Cl.⁷ .............................. G02B 26/08; G02B 5/08
(52) U.S. Cl. ........................ 359/224; 359/223; 359/846
(58) Field of Search ................................. 359/223, 224, 359/208, 846–848, 196

(56) References Cited

U.S. PATENT DOCUMENTS

| | | | | |
|---|---|---|---|---|
| 4,046,462 A | * | 9/1977 | Fletcher et al. | |
| 4,179,193 A | * | 12/1979 | Gillette et al. | |
| 4,639,100 A | | 1/1987 | Arnaud | |
| 4,657,358 A | | 4/1987 | Anthony et al. | |
| 4,934,803 A | | 6/1990 | Ealey | |
| 5,204,784 A | | 4/1993 | Spinhirne | |
| 5,471,341 A | | 11/1995 | Warde et al. | |
| 5,889,256 A | | 3/1999 | Osanai | |

FOREIGN PATENT DOCUMENTS

| | | |
|---|---|---|
| DE | 41 37 832 | 5/1993 |
| DE | 196 49 600 | 6/1997 |
| DE | 196 28 672 | 1/1998 |
| DE | 198 32 343 | 2/2000 |
| EP | 0 073 882 | 3/1983 |
| EP | 0 680 805 | 11/1995 |
| GB | 2 182 783 | 5/1987 |
| JP | 3 174995 | 7/1991 |

* cited by examiner

*Primary Examiner*—James Phan
(74) *Attorney, Agent, or Firm*—Oblon, Spivak, McClelland, Maier & Neustadt, P.C.

(57) ABSTRACT

The focal distance (f) of a laser (1) beam (2) is adjusted by projecting the beam (2) onto the center of a mirror (3) of variable curvature and controlled by a depression circuit or by electrostatic forces. Thus the focus (4) can be displaced in a direction which is inaccessible to the usual means such as turning but rigid mirrors.

5 Claims, 2 Drawing Sheets

SCANNING DEVICE FOR A LASER BEAM FOCUS

Figure 1:
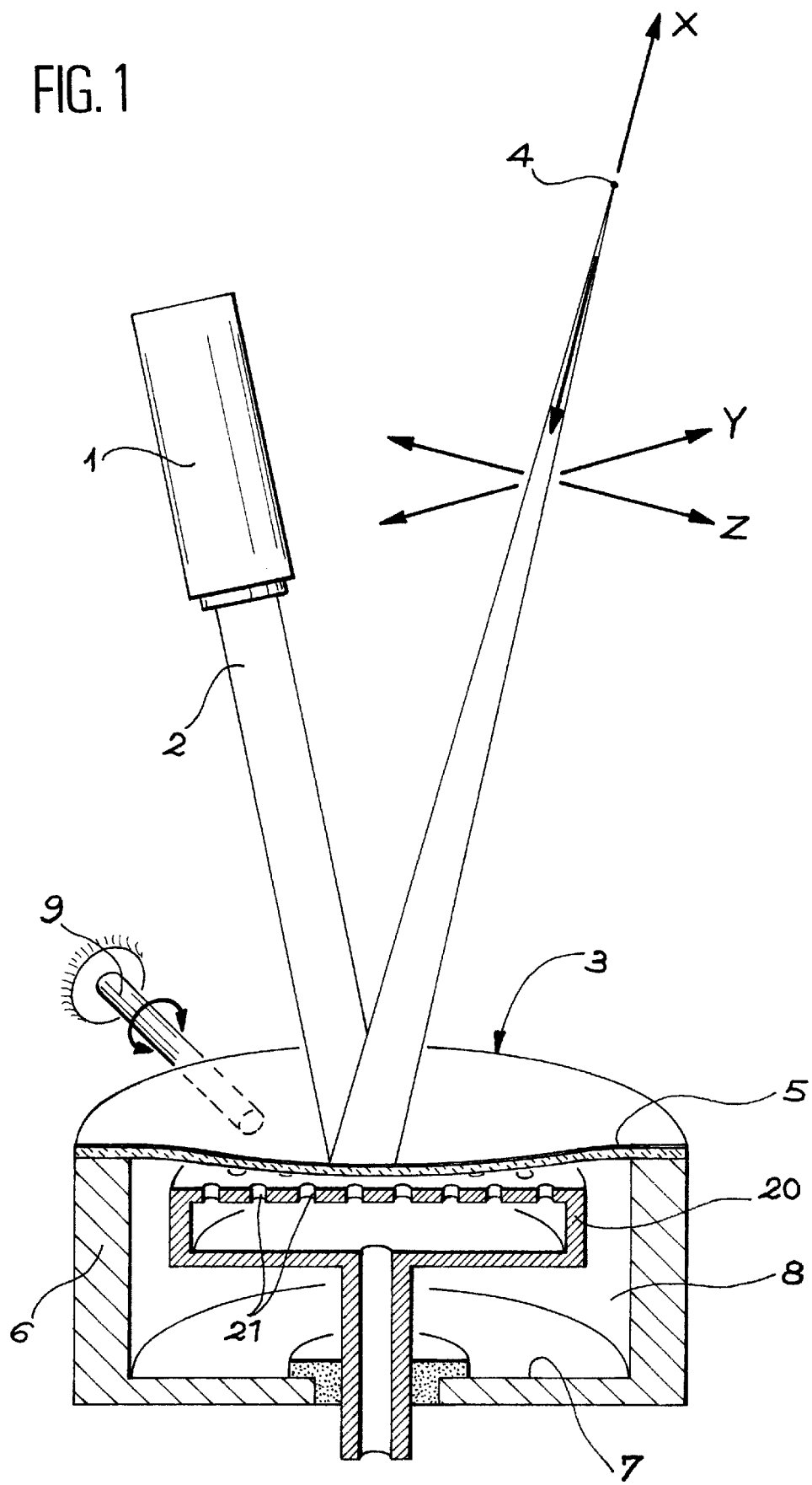

The invention relates to a device for sweeping a laser beam focus.

Power lasers make it possible to focus high luminous energy in a small volume focus and can be applied in physics to the study of particles, plasma confinement, machining, or surgical organic tissue section. Most of these applications involve moving the focus so that it sweeps across a trajectory, which is difficult to achieve in a simple way. Since the laser itself is voluminous, it is preferable to leave it immobile and to move the beam only. This is possible by passing it along an optic fibre, but not in all cases, and in particular not outside frequencies beyond the visible spectrum, whereas infrared lasers are greatly appreciated because of their power. Another means of displacing a beam consists of passing it by using a turning mirror, but movement of the focus in all directions can only be obtained by using a succession of mirrors turning around different axes, which poses considerable problems for coupling the position of the mirrors, since a rotation of one mirror necessitates displacing all the downstream mirrors so that the beam continues to pass between them. Furthermore, a large part of the energy is finally lost.

This is the reason why it is thus proposed to sweep a trajectory for a laser beam focus without moving the beam, but by modifying its focal distance. This is achieved by means of a variable curvature mirror, whose curvature variation is associated with a variation in the focusing of light beams; the flexibility of the membrane allows significant deformations and thus makes long sweepings possible. It should be noted that such mirrors are already known to those skilled in the art in telescopes or other optical devices, but herein the variation of focal length was used in particular to adjust the apparatus and to provide a clear image of a natural radiation (see French patent 2 662 512). The deformation is often controlled by networks of piezoelectric sensors whose displacements determine a two-dimensional profile of the membrane, but such actuators have only a small displacement range and their simultaneous control of different displacements is costly. They are poorly adapted for imposing regular curvatures (rather than local displacements), especially if the membrane is submitted to big overall displacements. An example of such prior art is given in U.S. Pat. No. 4,934,803-A.

To resume, the invention relates, in its most general form, to a device for sweeping a laser beam focus, comprising a flexible and stretched membrane onto which the beam is projected and reflected upstream from the focus, adjustable means for varying the curvature of the membrane and means for cooling the membrane. Greater possibilities for adjusting the focusing can be obtained if the means for varying the curvature are double and comprise a means for applying pressure distributed over the membrane and a means for applying pressure concentrated on the membrane. The means for distributed pressure application is a means for varying pressure from a closed chamber defined by the membrane, and the means for concentrated pressure application is an electrical circuit with a direct voltage generator between the membrane and an electrode adjacent to a central part of the membrane.

The means for cooling the membrane are essential for evacuating the incident heat from the laser. They can comprise means for blowing gas across a face of the membrane, and these means can consist of a circuit for renewal of the gaseous contents of the closed chamber.

Finally, devices for inclination of the membrane can allow adjustment of the orientation of the mirror and therefore the position of the focus of the beam in various directions.

Figure 2:
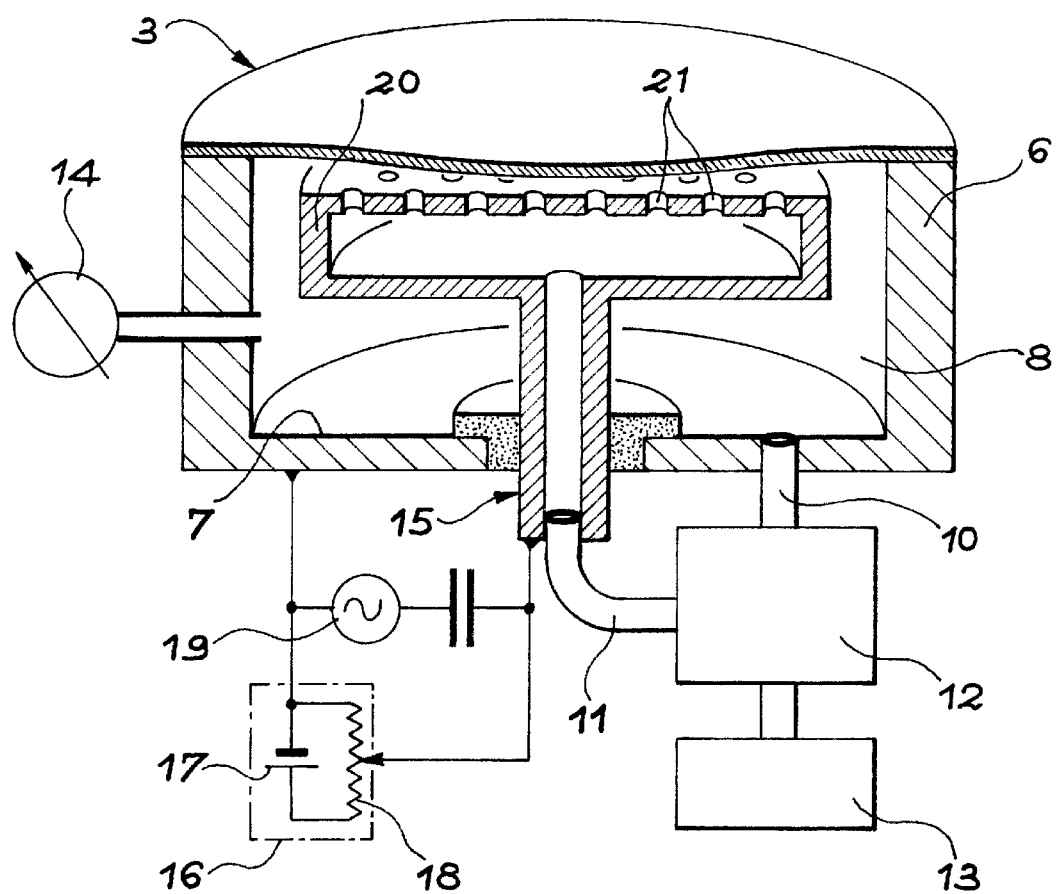
Figure 3:
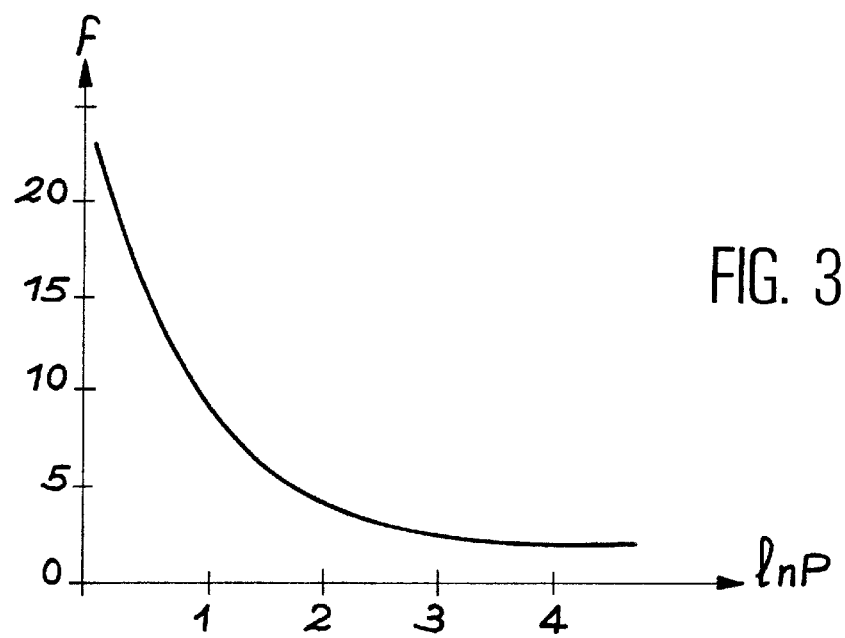

The invention will now be described in relation to the following figures which show a preferred embodiment:

FIG. 1 is a general view of the device,
FIG. 2 shows the mirror, and
FIG. 3 is a curve giving the experimental results.

FIG. 1 shows a laser 1 which projects a beam 2 towards a mirror 3 which reflects it and focuses it; the focus of the beam 2 is given the reference 4. The mirror 3 is a flexible membrane of small thickness, which can be made of metal, ceramic or composite material, possibly covered with a reflecting coating 5 on the face opposite the beam 2 if the base material itself is not so. Foil, metal-coated carbon, and alumina based ceramics can be suggested as examples, noting that the choice often depends on the wavelength of the reflected light. The membrane is stretched over a drum 6 which defines with it a base wall 7 of a closed chamber 8. Means described below and present mainly in the closed chamber 8 make it possible to modify the curvature of the mirror 3 and thus the distance of the focus 4, which sweeps the direction X the same as that of the beam 2 downstream from the mirror 3. Since the beam 2 is projected towards the centre of the membrane 3, whose average orientation does not vary, it is not deviated when the curvature of the mirror 3 is modified, but a deviation of the beam 2 in a perpendicular direction Y is possible by making the mirror 3 turn: the drum 6 is thus mounted on a rotational axle 9 passing through the centre of the mirror 3 and perpendicular to the direction Y. The axle 9 is driven by a motor, not shown. It is also possible to displace the beam 2 according to a third direction Z by mounting the mirror on a universal joint. There is no need to go into detail about such devices, which are known to those skilled in the art, for orienting plane mirrors, and therefore FIG. 2 is now described.

A delivery pipe 10 and a suction pipe 11 of a pump 12 connected to a cold source 13 open into the closed chamber 8; the air in the closed chamber 8 is recycled by the pump 12 where it is cooled, which maintains the contents of the closed chamber 8 together with the mirror 3, heated nonetheless by the beam 2, at an acceptable temperature. The pump 12 operates in a closed circuit and therefore has no influence on the pressure in the closed chamber 8. The same cannot be said of a second pump 14 which is adjustable and opens to the exterior in order to withdraw part of the contents of the closed chamber 8 and to submit it to a depression leading to indentation of the mirror 3. The adjustment of the depression by the pump 14 varies the curvature of the membrane, the focusing of the beam 2 and the position of the focus 4.

An analogous effect is obtained with an electrode 15 located opposite the centre of the membrane and which penetrates into the closed chamber 8 passing through the base wall 7. An electrical circuit 16 connects the electrode 15 to the mirror 3 through the intermediary of the base wall 7 and the drum 6. The electrical circuit 16 comprises a direct voltage generator 17, a rheostat 18 to vary the voltage applied to the terminals of the circuit, and a sine-wave voltage generator 19 in series with the former and which can be started or stopped by a switch, not shown. The electrostatic charges of opposite signs created by the generator 17 between the membrane and the electrode 15 also produce an attraction and curvature of the membrane. In practice, one can use either one or the other of these systems, but it should be noted that if the depression of the pump 14 is applied uniformly over the whole surface area of the membrane, the electrostatic forces tend to be concentrated in the centre of the membrane, which can produce a different deformation; depending on the case, one or other of these methods may be preferable or a combination of the two to obtain the best results. The means with the pump 14, which controls a regular curvature, will generally be preferred for providing more precise results, since the focusing will be independent of the place of reflection of the beam 2, but the electrode 15 can provide stronger localised focusing and may be preferred for extreme states of deformation of the mirror 3.

Another advantage of the double control means, especially with low inertia electrostatic control, is given below. The rheostat 18 makes it possible to vary the electrostatic attraction. Operation of the sine-wave voltage generator 19 produces a periodic variation of the quantity of electric charges and therefore oscillation of the mirror 3, welcome in certain applications such as welding thick parts, where the focus 4 moves to different depths of the joint.

The electrode 15 can be thin or, on the contrary, widened out into a plate 20, depending on whether one wishes to concentrate or distribute the forces evenly on the surface of the mirror 3; it can be hollow and act as an extension of one of the delivery and suction pipes 10 and 11; when the plate 20 exists, this is also hollow and provided with holes 21 for the passage of gas along its front face, which directs and distributes the cooling circuit efficiently onto the rear face of the mirror 3.

FIG. 3 shows the variations of a focal distance f in function of a depression P expressed in Napierian logarithms. It can be seen that the amplitude of the focal distance f, which can be applied between a null depression and a minimum asymptotic distance obtained at high depressions, is very high in relative value as in absolute value; the focal distance f is expressed in meters and was obtained with a drum of 30 mm diameter and a membrane of 0.5 mm thickness. Thinner membranes could make it possible to reduce the minimum focal distance even more.

The pressure or blowing of gas to create the curvature or the cooling can be applied to the external face of the mirror 3. It is possible to focus the beam 2 in a line instead of a point if the mirror 3 is lengthened and stretched between the two long sides of a rectangular frame replacing the circular drum 6.

The mirror 3 can be given other geometric shapes in function of the result to be obtained.

In the same way, it can be of variable thickness, for example thinner at the centre: the radius of curvature determining the focusing of the beam 2 is then smaller without the mechanical resistance of the mirror 3 being greatly affected.

Since the beam 2 generally only reaches a relatively small central portion of the mirror 3, whose curvature is almost uniform, the focusing is nearly perfect.

Other cooling circuits are possible as well as other fluids, and in particular liquids.

Finally, other means for deforming the mirror 3 can be envisaged, but means without solid contact are preferable and probably necessary for the curvature to be regular and without any significant coupling between the two means, whose actions can be adjusted independently and work together without any problems for the operator. Furthermore, the curvature of the mirror 3, which controls the focusing, cannot be controlled directly except through force fields or fluids, whereas solid activators generally control displacements.

What is claimed is:

1. Device for sweeping a laser beam focus, comprising a flexible and stretched membrane (3) onto which the beam (2) is projected and reflected upstream from the focus (4), adjustable means for varying the curvature of the membrane and means for cooling the membrane, characterised in that said means for varying the curvature are double and comprise means for applying pressure distributed over the membrane and means for applying pressure concentrated on the membrane, and the means for distributed pressure application is a means (14) for varying the pressure in a closed chamber (8) defined by the membrane, and the means for concentrated pressure application is an electrical circuit (16) with a direct voltage generator (17) between the membrane (3) and an electrode (15) adjacent to a central part of the membrane.

2. Device for sweeping a laser beam focus according to claim 1, characterised in that the electrical circuit further comprises an oscillating voltage generator between the membrane and the electrode.

3. Device for sweeping a laser beam focus according to claim 1, characterised in that the means for cooling the membrane comprise means for blowing gas in front of one face of the membrane.

4. Device for sweeping a laser beam focus according to claim 3, characterised in that the means for blowing gas comprise a circuit (10, 11, 12) for renewing the gaseous contents of the closed chamber (8).

5. Device for sweeping a laser beam focus according to claim 1, characterised in that it comprises a device (9) for orientation of the membrane.

* * * * *